US012690792B2

(12) United States Patent     (10) Patent No.:   US 12,690,792 B2

Nikula et al.     (45) Date of Patent:     Jul. 28, 2026

(54) BIO-SIGNAL APPARATUS, OPERATION METHOD OF BIO-SIGNAL APPARATUS AND MANUFACTURING METHOD OF BIO-SIGNAL APPARATUS

(71) Applicant: BITTIUM BIOSIGNALS OY, Kuopio (FI)

(72) Inventors: Arto Nikula, Oulu (FI); Juha Myllykangas, Kuopio (FI)

(73) Assignee: BITTIUM BIOSIGNALS OY, Kuopio (FI)

( * ) Notice: Subject to any disclaimer, the term of this patent is extended or adjusted under 35 U.S.C. 154(b) by 1122 days.

(21) Appl. No.: 17/735,544

(22) Filed: May 3, 2022

(65) Prior Publication Data

US 2023/0355153 A1     Nov. 9, 2023

(51) Int. Cl.
    *A61B 5/00*     (2006.01)
    *A61B 5/05*     (2021.01)
    (Continued)

(52) U.S. Cl.
    CPC .............. *A61B 5/273* (2021.01); *A61B 5/256* (2021.01); *A61B 5/6813* (2013.01);
    (Continued)

(58) Field of Classification Search
    CPC ..... A61B 5/282; A61B 5/6824; A61B 5/0006; A61B 5/1118; A61B 2560/0412;
    (Continued)

(56) References Cited

U.S. PATENT DOCUMENTS 6,475,043 B2 * 11/2002 Pereira ................... H01R 4/028
                                          439/876
7,286,865 B2 * 10/2007 Nazeri ................... A61B 5/282
                                          600/382

(Continued)

FOREIGN PATENT DOCUMENTS

EP        1 062 908       12/2000
WO     2011/033632       3/2011

OTHER PUBLICATIONS

Sep. 11, 2023 Search Report issued in European Patent Application No. 23170572.4, pp. 1-8.

(Continued)

*Primary Examiner* — Joseph A Stoklosa
*Assistant Examiner* — Brian M Antiskay
(74) *Attorney, Agent, or Firm* — Nixon & Vanderhye PC

(57)          ABSTRACT

A bio-signal apparatus comprises a first connection part, a second connection part and a seal. The first connection part comprises a sheet, which carries a patch electrode structure and comprises electrodes for reception of a bio-signal from a body of a mammal and first electrical connectors, the first electrical connectors being electrically connected with the electrodes. The second connection part comprises counterpart electrical connectors, and the first electrical connectors and the counterpart electrical connectors being repeatedly attachable and releasable with each other for transferring the bio-signal therethrough to data processing. The seal seals an interface of the first connection part and the second connection part against dust and moisture, and the seal surrounds the first electrical connectors and the electrical counterpart electrical connectors in a continuous manner.

19 Claims, 7 Drawing Sheets

(51) Int. Cl.

| | |
|---|---|
| *A61B 5/25* | (2021.01) |
| *A61B 5/256* | (2021.01) |
| *A61B 5/273* | (2021.01) |
| *H01R 12/70* | (2011.01) |
| *H01R 13/52* | (2006.01) |
| *H01R 13/623* | (2006.01) |

(52) U.S. Cl.

CPC ....... *A61B 5/6831* (2013.01); *H01R 12/7076* (2013.01); *H01R 12/7082* (2013.01); *H01R 13/5219* (2013.01); *H01R 13/623* (2013.01); *A61B 2562/125* (2013.01); *H01R 2201/12* (2013.01)

(58) Field of Classification Search

CPC ......... A61B 5/6833; A61B 5/25; A61B 5/318; A61B 5/308; A61B 2560/0468; A61B 5/287; A61B 5/6804; A61B 5/4806; G16H 40/67; G16H 20/30

USPC .......................... 600/372, 382–393, 508–509

See application file for complete search history.

(56) References Cited

U.S. PATENT DOCUMENTS

| | | | | |
|---|---|---|---|---|
| 9,655,537 | B2 * | 5/2017 | Bardy | ................... A61B 5/333 |
| 2007/0106167 | A1 | 5/2007 | Kinast | |
| 2008/0288026 | A1 * | 11/2008 | Cross | ................. H01R 13/5224 |
| | | | | 607/60 |
| 2012/0089037 | A1 * | 4/2012 | Bishay | ................... A61B 5/335 |
| | | | | 600/509 |
| 2012/0330126 | A1 * | 12/2012 | Hoppe | .............. A61B 5/14552 |
| | | | | 600/300 |
| 2016/0186792 | A1 * | 6/2016 | Valencia | .............. F16B 7/0406 |
| | | | | 403/349 |
| 2016/0359150 | A1 * | 12/2016 | de Francisco Martin | .................. |
| | | | | A61B 5/282 |
| 2020/0315524 | A1 | 10/2020 | Bardy et al. | |
| 2021/0128042 | A1 * | 5/2021 | Herberger | .......... H01R 13/6278 |
| 2022/0039719 | A1 | 2/2022 | Abercrombie, II et al. | |

OTHER PUBLICATIONS

Smith et al., "Dimensional Data on Vulva Vaginal Anatomy: Medical Device Design Barrier," Proceedings of the 2020 Design of Medical Devices Conference, DMD2020, April 6, 7-9, 2020, Minneapolis, MN, USA, pp. 1-7.

* cited by examiner

BIO-SIGNAL APPARATUS, OPERATION METHOD OF BIO-SIGNAL APPARATUS AND MANUFACTURING METHOD OF BIO-SIGNAL APPARATUS

FIELD

The invention relates to a bio-signal apparatus, an operation method of a bio-signal apparatus and a manufacturing method of a bio-signal apparatus.

BACKGROUND

An electronic device, which measures bio-signals such as ECG (ElectroCardioGram) and EEG (ElectroEncephalo-Gram), must be well contacted with the electrodes that are in contact with the body and mechanically reliably fixed to its support. At least some kind electromechanical part is used for connecting and attaching a non-disposable bio-signal measurement device with a disposable single-use patch electrode arrangement, and the electromechanical part is structurally and/or electrically rather complicated. It may also contain metal parts or even some assembled electrical connector to interface with the non-disposable bio-signal measurement device. Because of that, it may even be the most expensive part to manufacture and assemble on the disposable patch electrode arrangement.

BRIEF DESCRIPTION

The present invention seeks to provide an improvement to the electromechanical connection.

The invention is defined by the independent claims. Embodiments are defined in the dependent claims.

If one or more of the embodiments is considered not to fall under the scope of the independent claims, such an embodiment is or such embodiments are still useful for understanding features of the invention.

LIST OF DRAWINGS

Example embodiments of the present invention are described below, by way of example only, with reference to the accompanying drawings, in which FIGS. 1A and 1C illustrate an example of a bio-signal measurement apparatus;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment.

The articles "a" and "an" give a general sense of entities, structures, components, compositions, operations, functions, connections or the like in this document. Note also that singular terms may include pluralities.

Single features of different embodiments may also be combined to provide other embodiments. Furthermore, words "comprising" and "including" should be understood as not limiting the described embodiments to consist of only those features that have been mentioned and such embodiments may also contain features/structures that have not been specifically mentioned. All combinations of the embodiments are considered possible if their combination does not lead to structural or logical contradiction.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signals used for measurement and/or the control are irrelevant to the actual invention. Therefore, they need not be discussed in more detail here.

Figures 1A, 1B:
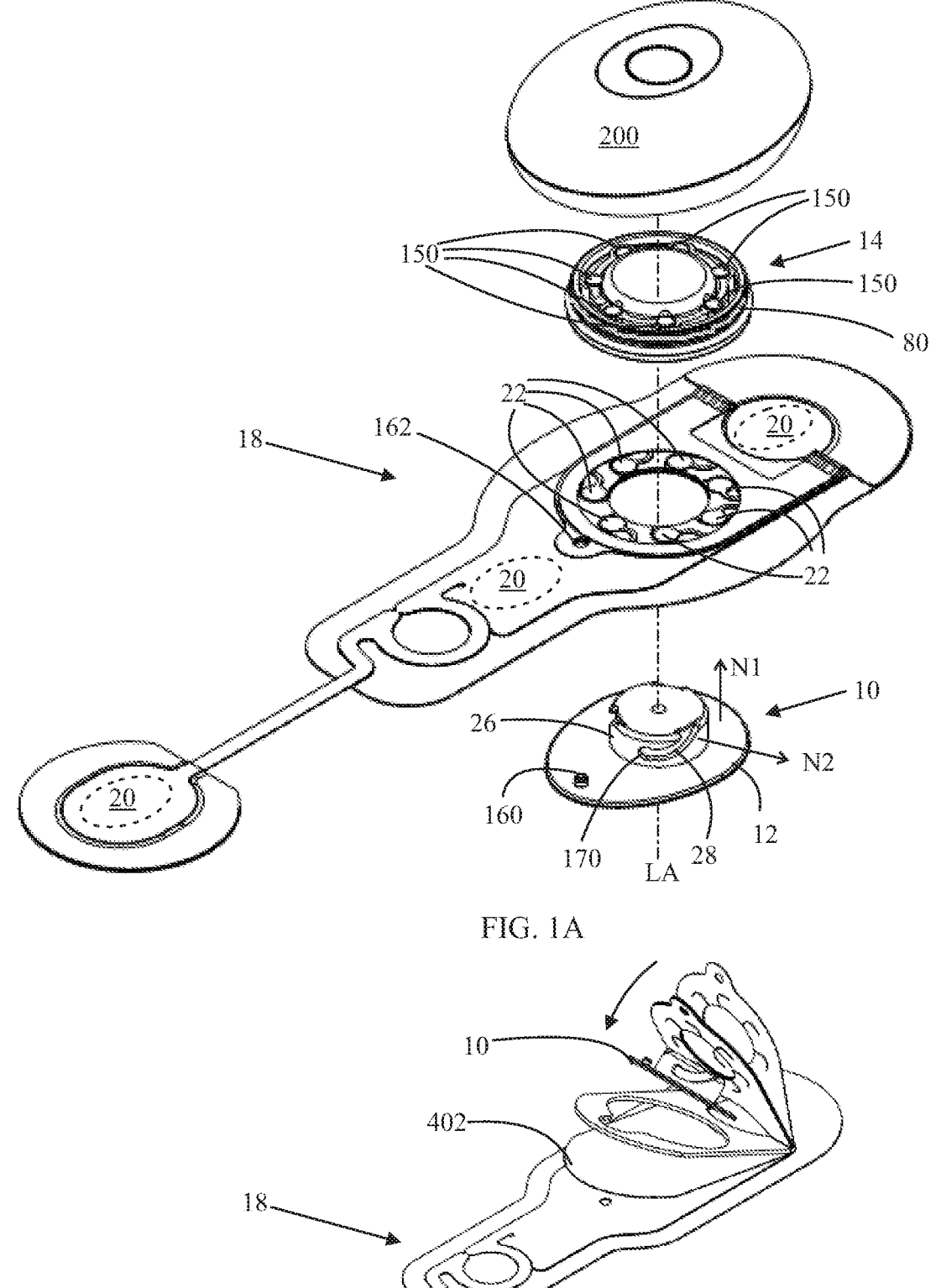
FIG. 1B illustrates an example of a potential location of a first connection part relating to a patch electrode structure.
Figures 1C, 2:
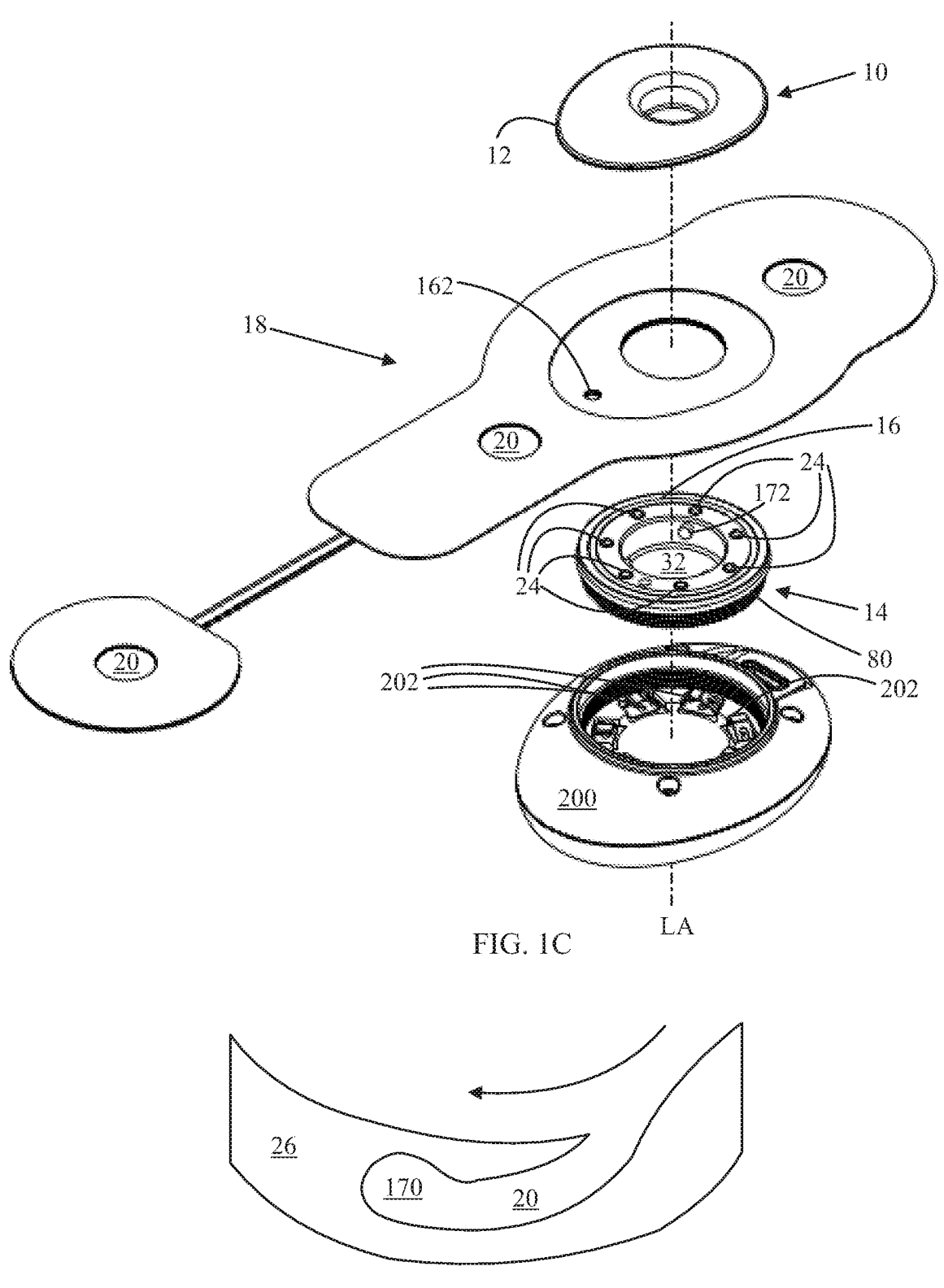
FIG. 2 illustrates an example of a helical groove of a cylinder extension.

FIG. 1A and FIG. 1C illustrate an example of a bio-signal apparatus that comprises a first connection part 10 and a second connection part 14 and a seal 16 (the seal is shown in FIG. 1C). The bio-signal is an electrical signal formed by the nervous system of a mammal 100 and hence it may also be called a bioelectrical signal. The first connection part 10 comprises a sheet 12 of electrically non-conductive material. The sheet 12 may also be considered a plate or the like at least in some embodiments. The sheet 12 may be made of electrically non-conductive polymer such as plastic. However, the sheet 12 may be of other kind of material and even electrically conductive.

The sheet 12 carries a patch electrode structure 18, which comprises patch electrodes 20 for reception of a bio-signal from a body of a mammal 100. In this application, the term "carry" may mean to support, hold, comprise, include or contain. The patch electrode structure 18 also comprises first electrical connectors 22, which are electrically connected with the electrodes 20 through electrical conductors of the patch electrode structure 18. The electrical conductors of the patch electrode structure 18 are not shown in FIG. 1 because a person skilled in the art is familiar with a patch electrode structure, per se.

The patch electrode structure 18 is typically a piece of sheet that may be narrow like a band or broad like a wide planar surface and it is often fairly thin and flexible. Thickness of the patch electrode structure 18 may resemble those of sheet of plastic, paper, board or cloth. The patch electrode structure 18 is configured to be in contact with skin or mucous membrane of a mammal 100 such as a human being for a bio-signal measurement. The bio-signal may be related to body movement, body temperature, heart rate variability, electrocardiogram, electromyogram, electroencephalogram or the like for example. During a measurement, the patch electrode structure 18 feeds directly or indirectly electrical bio-signals to a non-disposable bio-signal receiving unit 200 that is separate from the patch electrode structure 18. The disposable patch electrode structure 18 may have a PET-layer.

The second connection part 14 may be of electrically non-conductive material and comprises counterpart electrical connectors 24. The first electrical connectors 22 and the counterpart electrical connectors 24 are repeatedly attachable and releasable with each other for transferring bio-signal data therethrough to data processing. The electric connection may also connect the first and second connection part 10, 14 together mechanically.

The seal 16 is configured to seal an interface of the first connection part 10 and the second connection part 14 against dust and moisture. The seal 16 surrounds the first electrical connectors 22 and the electrical counterpart electrical connectors 24 in a continuous manner in order to protect the electrical connectors and the electrical counterpart connectors 22, 24. The seal 16 seals a potential gap between the first connection part 10 and the second connection part 14.

Figure 4A:
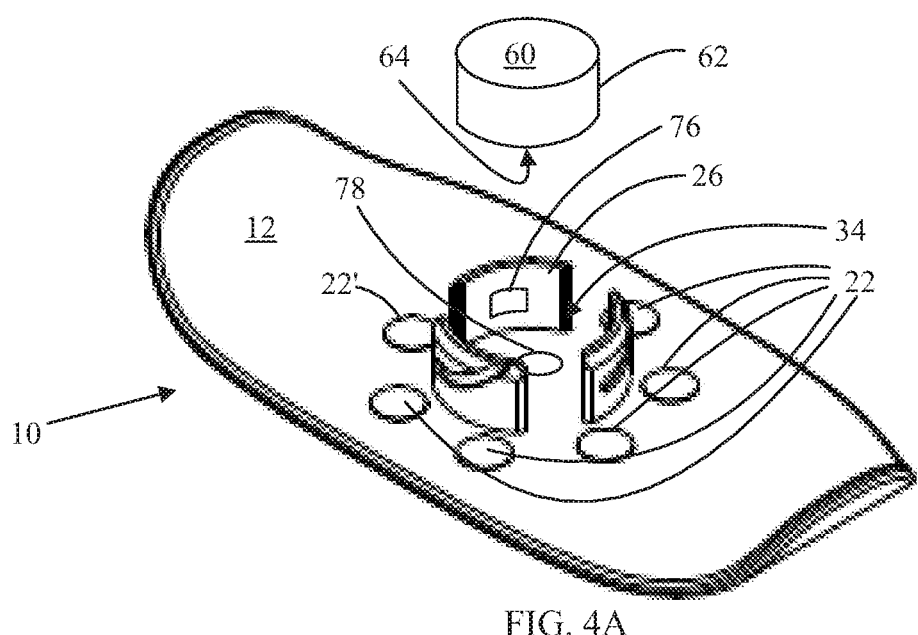
FIGS. 4A and 4B illustrate an example of a first connection part of the bio-signal apparatus, which is suitable for keeping the electrodes against skin with fingers.
Figure 5:
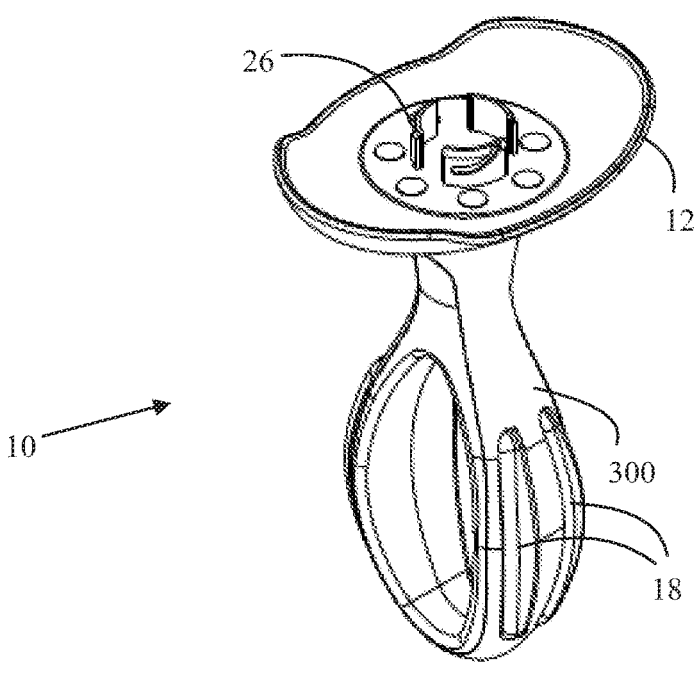
FIG. 5 illustrates an example of an extension for measurement of pelvic bottom muscles.

In embodiment examples of which are illustrated in FIGS. 1A, 4A and 5, the sheet 12 comprises a cylinder or rod extension 26. The extension 26 of the first connection part 10 has a longitudinal axis LA substantially parallel to a normal N1 of a surface of the sheet 12 at a location of the extension 26 of the first connection part 10. An outer surface 30 of said extension 26 has at least one helical groove 28, a normal N2 of the outer surface 30 pointing in a direction orthogonal to the normal N1. The outer surface 30 comprise curved parts of a circle as a wall of the cylinder or rod, or the wall may be continuous.

The second connection part 14 comprises a cylindrical counterpart structure 32 to the extension 26 of the first connection part 10 and to the at least one helical groove 28. The counterpart structure 32 may be made of electrically non-conductive material without limiting to this. The first connection part 10 and the second connection part 14 are repeatedly attachable and releasable with each other in a rotatable manner based on the at least one helical groove 28 and its counterpart.

In an embodiment an example of which is shown in FIGS. 1A and 1n more details in FIG. 2, the helical groove 28 of the extension 26 of the first connection part 10 may comprise a locking structure 170 at an end of the helical groove 28 in a fastening direction of the helical groove 28 (the fastening direction is shown with an arrow in FIG. 2). The counterpart structure 32 included in the second connection part 14 may comprise at least one pin 172 as shown in FIG. 1C. The at least one pin 172 moves in the helical groove 28 when the first connecting part 10 and the second connecting part 14 are touching each other in an aligned manner and the first connecting part 10 and the second connecting part 14 are rotated with respect to each other. The at least one pin 172 locks the first connection part 10 and the second connection part 14 together when the pin 172 is within the locking structure 170. The locked state of the first connection part 10 and the second connection part 14 can be opened manually such that the first connection part 10 and the second connection part 14 are pushed toward each other and simultaneously the first connection part 10 and the second connection part 14 are turned to a direction opposite to the fastening direction. The locking structure 170 may comprise a widening of the groove 28 and/or a decrease of an angle of a pitch of the helical groove 28, for example. The elastic structure 402 may help the pin 172 to remain in the locking structure 170 (see FIG. 6).

Figures 3A, 3B:
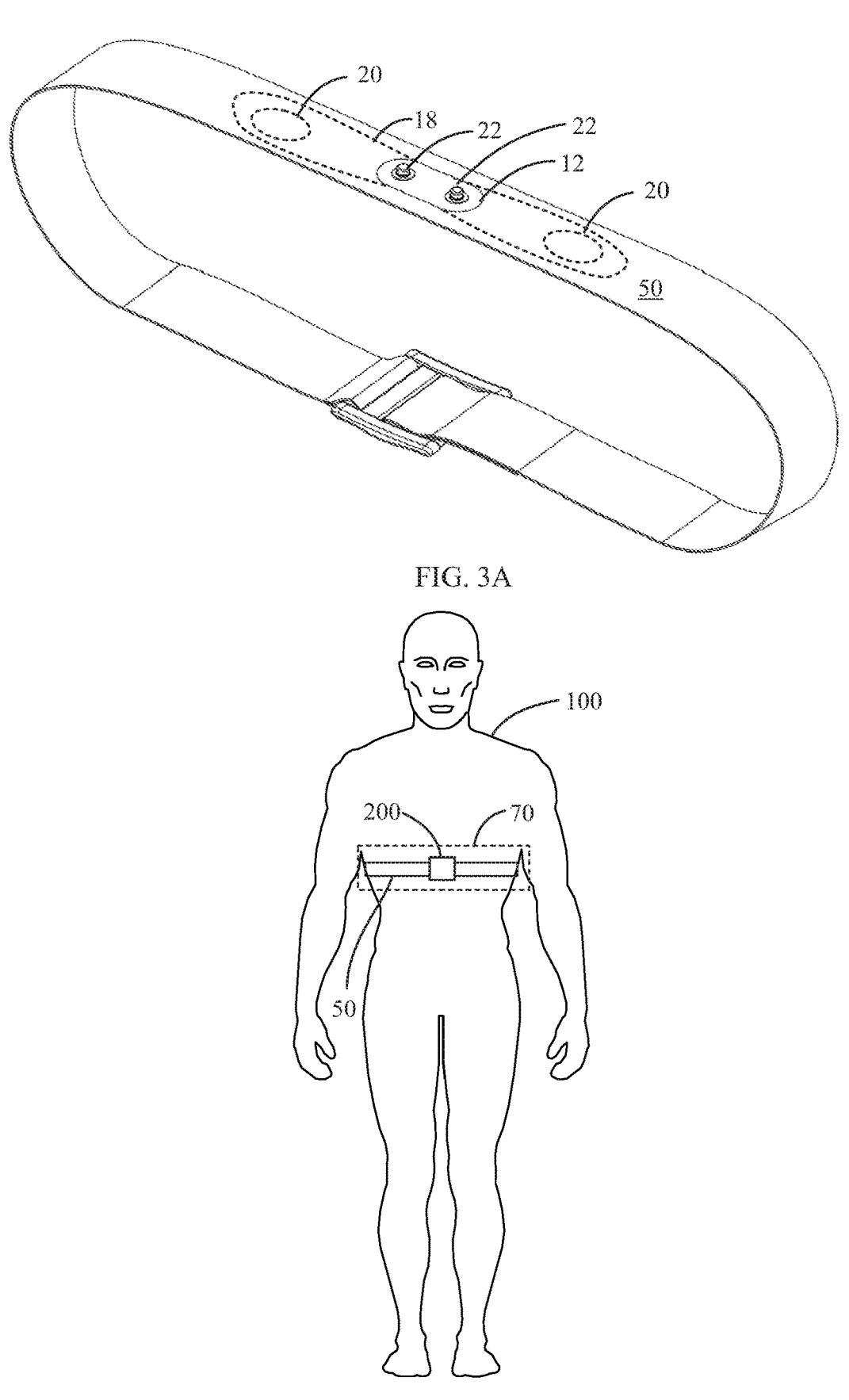
FIGS. 3A and 3B illustrate an example of a belt with the bio-signal measurement apparatus, the belt being attachable round a body part.

In an embodiment an example of which is illustrated in FIGS. 3A and 3B, the sheet 12 may be structurally integrated with a band 50 attachable round a body part 70 of the mammal 100. The band 50 may comprise the patch electrode structure 18 for measuring the bio-signal from the body part 70. The body part 70 may be a chest, for example.

In an embodiment an example of which is illustrated in FIG. 4, the extension 26 of the first connection part 10 may comprise a cavity 34, which receives, keeps and releases a battery 60. The cavity 34 then includes an electrical cavity conductor 76, which couples a terminal 62 of the battery 60 with an electrical connector 22' of the first electrical connectors 22. The first connection part 10 or the second connection part 14 may comprise a connection part conductor 78 electrically coupled with another terminal 64 of the battery 60 (in FIG. 4A the first connection part 10 comprises the connection part conductor 78). The cavity conductor 76 and the connection part conductor 78 are electrically connected with an electrical circuit of at least one of the first connection part 10 and the second connection part 14 for supplying electric energy (the electric circuit of the first connection part 10 and the second connection part 14 are not shown in Figs.).

In an embodiment example of which is illustrated in FIGS. 1A and 1C, the second connection part 14 may comprise a physical connection mechanism 80 and second electrical connectors 150 electrically coupled with the counterpart electrical connectors 24. The physical connection mechanism 80 may comprise thread, for example. The bio-signal apparatus comprises a bio-signal receiving unit 200, which comprises receiving unit electrical connectors 202. The physical connection mechanism 80 is configured to allow replacement of the connection part 14 or the bio-signal receiving unit 200. The receiving unit electrical connectors 202 are counter-connectors to the second electrical connectors 150. The second electrical connectors 150 and the receiving unit electrical connectors 202 may transfer the bio-signal to an electric circuit of the bio-signal receiving unit 200 for storing the bio-signal in at least one memory of the bio-signal receiving unit 200 (the electric circuit of the bio-signal receiving unit 200 is not shown in Figs). The second electrical connectors 150 and the receiving electrical connectors 202 may also transfer electric energy of the battery 60 for electric operation of at least part of the electric circuits of the bio-signal measurement device.

In an embodiment, the bio-signal receiving unit 200 may comprise a non-disposable bio-signal measurement device that have at least one processor and memory for data processing. In an embodiment, the bio-signal receiving unit 200 may be connected in a wired manner or in a wireless manner with a separate bio-signal measurement device. Still alternatively, the bio-signal receiving unit 200 may be a part of the bio-signal measurement device with or without wires. The wired connection between the bio-signal receiving unit 200 and the bio-signal measurement device may be realized through an USB-connector (USB=universal serial bus) or the like. However, the bio-signal receiving unit 200 may only connect with the disposable patch electrode structure 10 and may output the processed bio-signal information. The bio-signal receiving unit 200 may store the bio-signal temporally or permanently. The bio-signal receiving unit 200 may overwrite an earlier stored bio-signal.

Figure 4B:
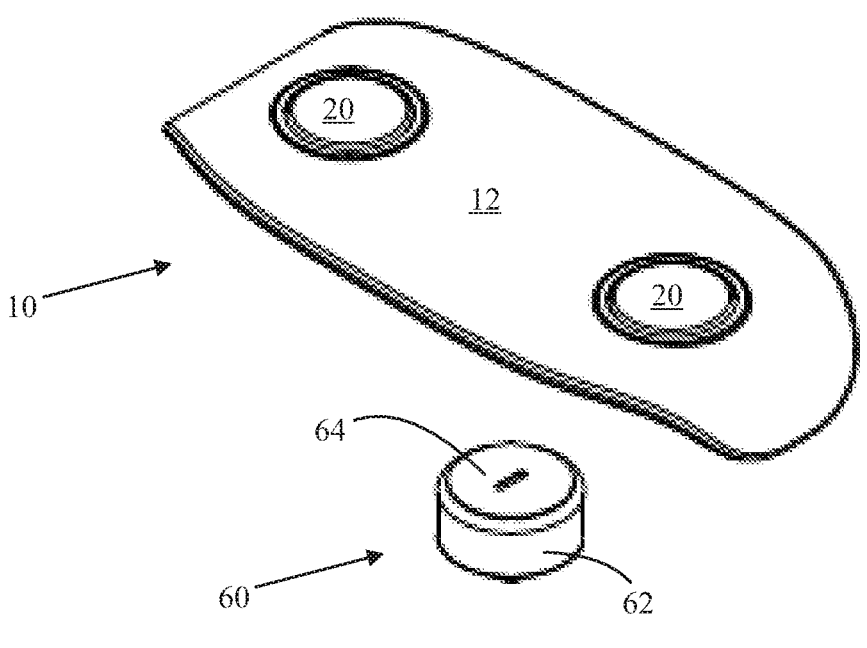

In an embodiment an example of which is illustrated in FIGS. 4A and 4B, the patch electrode structure 18 may be structurally integrated with the sheet 12 of the first connection part 10. The sheet 12 may be oblong with tip and tail curved in direction parallel to the normal N1 of the sheet 12, the normal N pointing toward the counterpart electrical connectors 24. The sheet 12 of FIGS. 4A and 4B which could be understood the plate can easily be pressed against skin with fingers, for example.

In an embodiment an example of which is illustrated in FIG. 5, the sheet 12 of the first connection part 10 comprises a longitudinal extension 300 anatomically fitted to a vagina. The fitting may be based on a standard anatomical vagina. The longitudinal extension 300 carries the patch electrode structure 18 for receiving a bio-signal from pelvic floor muscles of the mammal 100.

In an embodiment an example of which is illustrated in FIG. 1, the sheet 12 may comprise at least one locking pin 160 and the patch electrode structure 18 has a corresponding hole 162 for each of the at least one locking pin 160. Each of the at least one locking pin 160 is inserted in a corresponding hole 162 of the at least one hole 162 for aligning and keeping the sheet 12 and the patch electrode structure 18 in a desired and/or suitable position with respect to each other in response to the first connection part 10 and the second connection part 14 being fastened together. The at least one locking pin 160 may extend upto the bio-signal receiving unit 200 which has a corresponding locking hollow (not shown in Figs). When the at least one pin 160 enters the corresponding hollow, the parts of whole apparatus become immobile with respect to each other which makes the apparatus firm and easy to use and keep the apparatus in hand. The second connection part 14 also allows the locking to be opened which in turn allows exchange of any of the detached parts.

Figure 6:
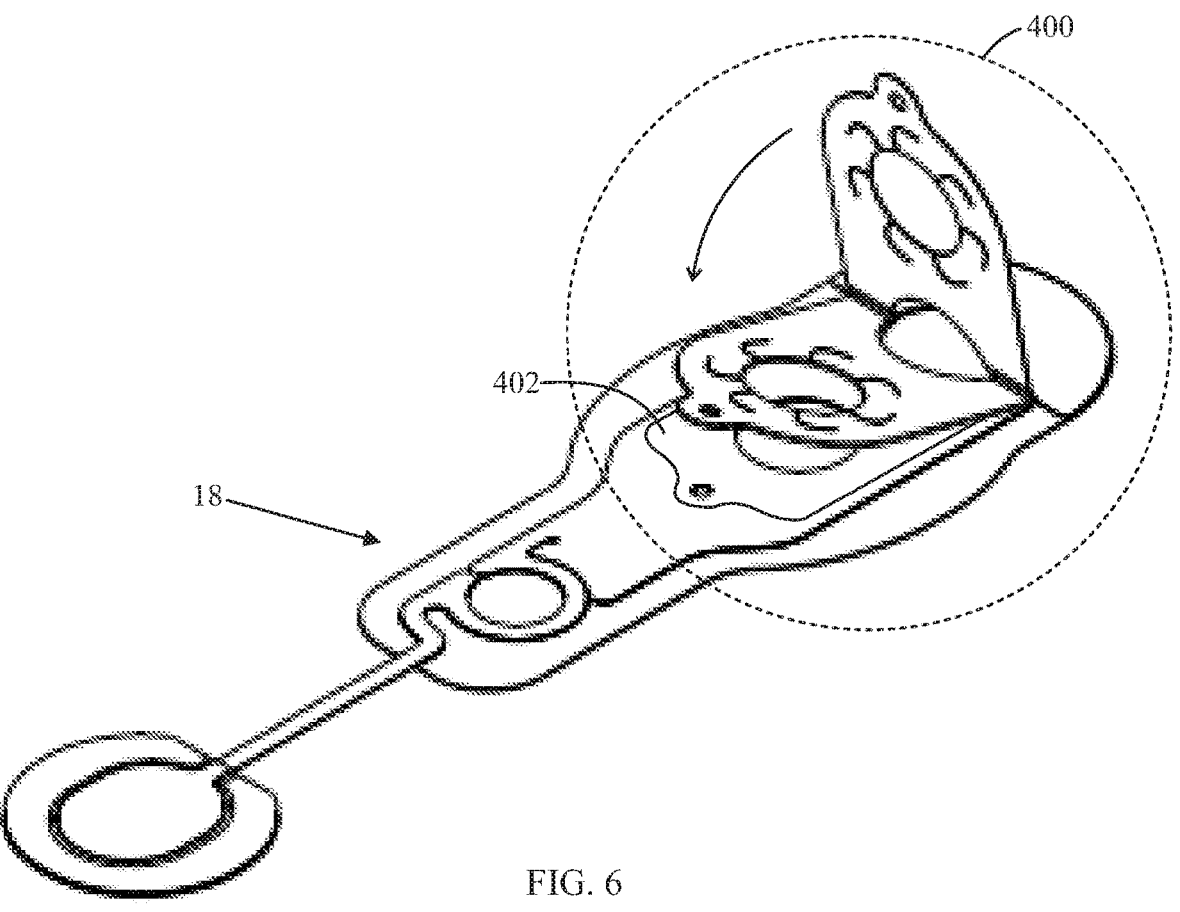
FIG. 6 illustrates an example of folded electrode structure.

In an embodiment an example of which is illustrated in FIGS. 1B and 6, the patch electrode structure 18 comprises a folded section 400, which comprises an elastic structure 402 within the folded section 400 for causing a spring force to attachment of the first connection part 10 and the second connection part 14. The folded section 400 is formed such that a sheet structure at one end of the patch electrode structure 18 is folded over such so that one part of the electrode structure 18 is positioned on top of another part. The elastic structure 402 is inserted between the parts positioned on each another. The elastic structure 402 may be made of plastic, for example. The elastic structure 402 may comprise soft polymer foam, which is compressible, and the soft polymer responds to force compressing it with a force of the same magnitude but of opposite direction. That is, the soft polymer provides a force as a function of the compression.

FIG. 1B illustrates an example of a potential location of the first connection part 10 relating to the patch electrode structure 18. In FIG. 1A, the first connection part 10 is in contact with an outer surface of the patch electrode structure 18. In FIG. 1B, the first connection part 10 is inserted within the folded section 400 such that the extension 26 of the first connection part 10 extends through the patch electrode structure 18 of the folded section 400.

Figure 7:
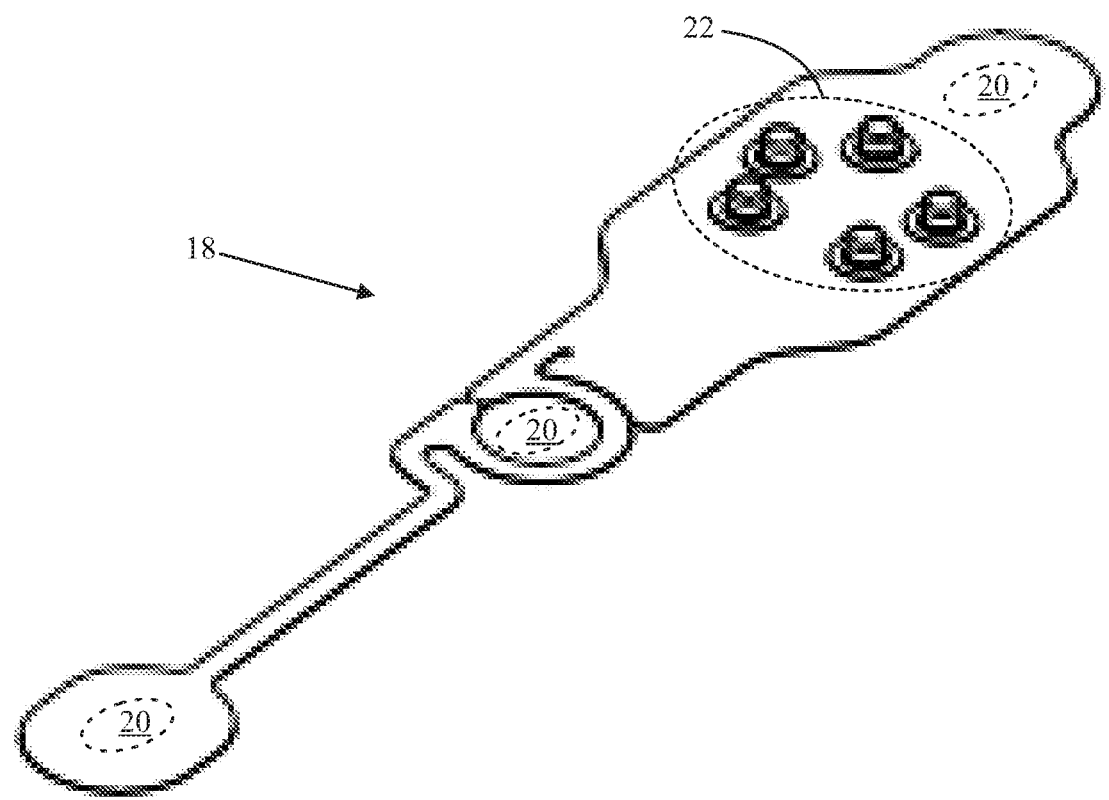
FIGS. 7 and 8 illustrate an example of a pair of quick-release connectors.

In an embodiment an example of which is illustrated in FIG. 7, the patch electrode structure 18 may comprise quick-release fasteners as the first electrical connectors 22. The quick-release fasteners can be repeatedly fastened and released with their counterparts. The quick-release fasteners may be tool-less connectors. The quick-release fasteners can be connected to and disconnected from each other using a finger force applied thereto by fingers of a person. Correspondingly, quick-release fasteners can be connected to and disconnected from their counterparts using a finger force applied thereto by fingers of a person. That is why it is question of quick-release fasteners. The quick-release fasteners and their counterparts may be snap-together-fastener pairs.

Figure 8:
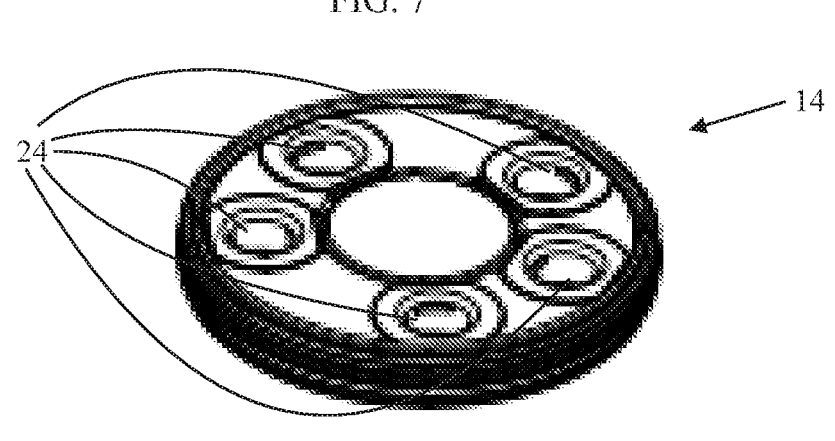

FIG. 8 illustrates an example of the counterparts of the first electrical connectors 22. The counterparts are the quick-release fasteners of the second connection part 14 and they are the counterpart electric connectors 24.

Figure 9:
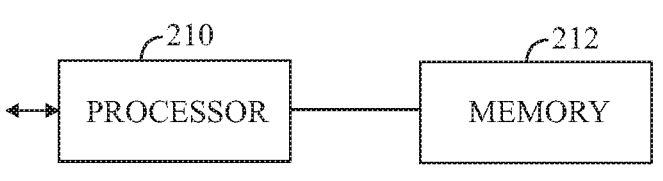
FIG. 9 illustrates an example of a data processing unit of the bio-signal receiving unit.

FIG. 9 illustrates an example of a data processing unit of the bio-signal measurement apparatus. The electric apparatus then comprises one or more processors 210 and one or more memories 212 including computer program code. The one or more memories 212 and the computer program code may be configured to, with the one or more processors 210, cause the bio-signal measurement apparatus at least to receive bio-signal from the patch electrode structure 18 and perform data processing of the bio-signal.

Figures 10, 11:
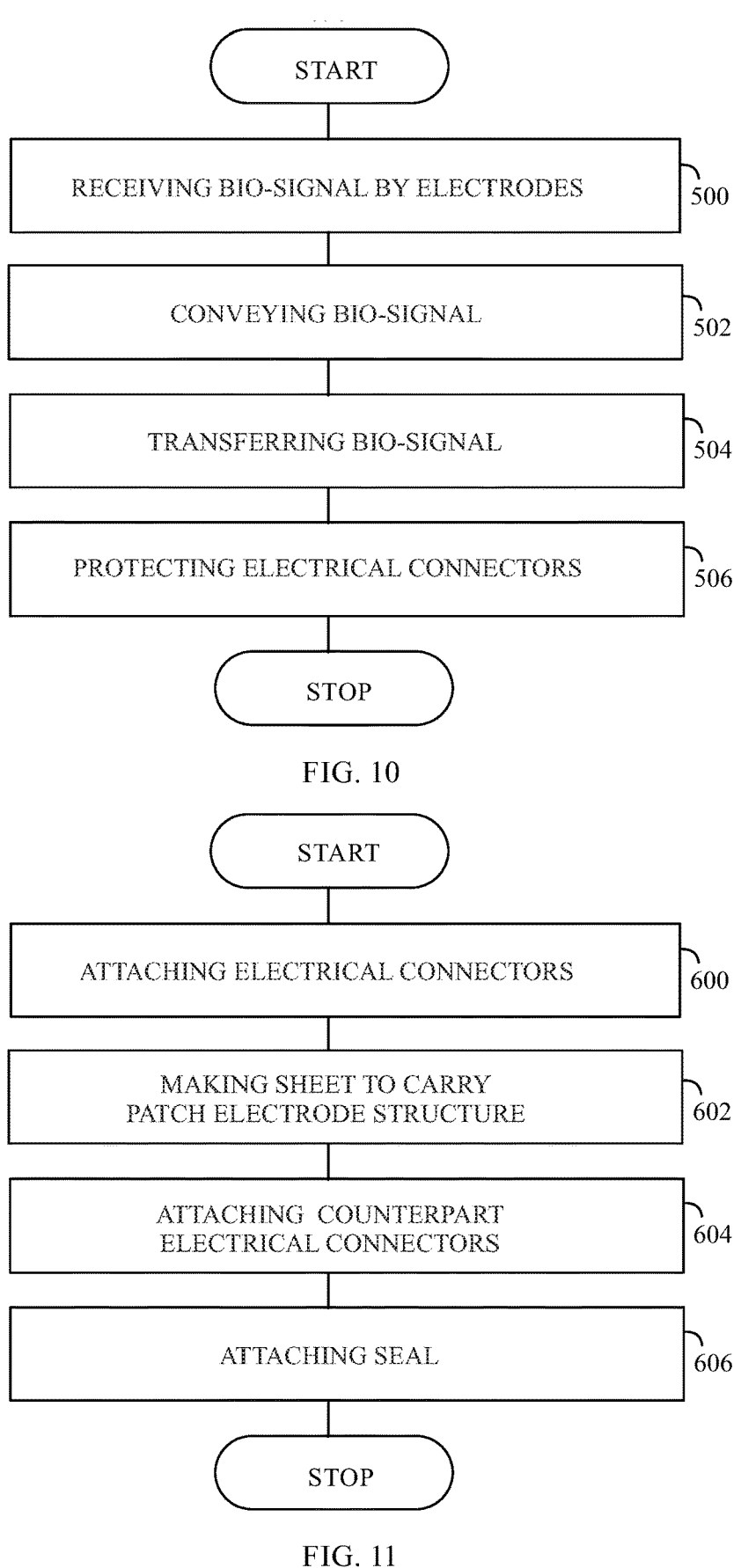
FIG. 10 illustrates an example of a flow chart an operation method.
FIG. 11 illustrates of an example of a flow chart of a manufacturing method.

FIG. 10 is a flow chart of an operation method of a bio-signal apparatus. In step 500, a bio-signal is received from a body 102 of a mammal 100 by electrodes 20 of a patch electrode structure 18 that is carried by a sheet 12.

In step 502, the bio-signal is conveyed to first electrical connectors 22 of a first connection part 10, the first electrical connectors 22 being electrically connected with the electrodes 20.

In step 504, the bio-signal is transferred from the first electrical connectors 22 to counterpart electrical connectors 24 of a second connection part 14, the first electrical connectors 22 and the counterpart electrical connectors 24 being repeatedly attachable and releasable with each other for transferring the bio-signal therethrough to data processing.

In step 506, the first electrical connectors 22 and the second electrical connectors 24 are protected with a seal 16, which seals an interface of the first connection part 10 and the second connection part 14 against dust and moisture, and the seal 16 surrounds the first electrical connectors 22 and the electrical counterpart electrical connectors 24 in a continuous manner.

FIG. 11 is a flow chart of a manufacturing method of a bio-signal apparatus. In step 600, first electrical connectors 22 are attached to a patch electrode structure 18 that comprises electrodes 20 for reception of a bio-signal from a body 102 of a mammal 100, the first electrical connectors 22 being electrically connected with the electrodes 20.

In step 602, a sheet 12 is made to carry the patch electrode structure 18 for realizing a first connection part 10, In step 604, counterpart electrical connectors 24 are attached to a second connection part 14, the first electrical connectors 22 and the counterpart electrical connectors 24 being repeatedly attachable and releasable with each other for transferring the bio-signal therethrough.

In step 606, a seal 16 is attached to the first connection part 10 or the second connection part 14 for protecting the electrical connectors of the first connection part 10 and the second connection part 14 against dust and moisture, and the seal 16 surrounding the first electrical connectors 22 and the electrical counterpart electrical connectors 24 in a continuous in response to attachment of the first connection part 10 and the second connection part 14 with each other.

It will be obvious to a person skilled in the art that, as technology advances, the inventive concept can be implemented in various ways. The invention and its embodiments are not limited to the example embodiments described above but may vary within the scope of the claims.

What is claimed is:

1. A bio-signal apparatus, comprising:

a first connection part, a second connection part and a seal; wherein:

the first connection part comprises a sheet;

the sheet is configured to carry a patch electrode structure, which comprises electrodes configured to receive a bio-signal from a body of a mammal and first electrical connectors, the first electrical connectors being electrically connected with the electrodes;

the second connection part comprises counterpart electrical connectors, the first electrical connectors and the counterpart electrical connectors being repeatedly attachable and releasable with each other to transfer the bio-signal therethrough to data processing;

the seal is configured to seal an interface of the first connection part and the second connection part against dust and moisture, and the seal is configured to surround the first electrical connectors and the electrical counterpart electrical connectors in a continuous manner; and the second connection part comprises a physical connecting mechanism and second electrical connectors electrically coupled with the counterpart electrical connectors, and the bio-signal apparatus comprises a bio-signal receiver, which comprises receiver electrical connectors, which are counter-connectors to the second electrical connectors, and the second electrical connectors and the receiver electrical connectors are configured to transfer the bio-signal to an electric circuit of the bio-signal receiver to store the bio-signal in at least one memory of the bio-signal receiver.

2. The bio-signal apparatus of claim 1, wherein the sheet comprises a cylinder or rod extension, and at least one helical groove on an outer surface of the cylindrical or rod extension, the cylinder or rod extension having a longitudinal axis substantially parallel to a normal of a surface of the sheet;

the second connection part comprises a cylindrical counterpart structure to the cylinder or rod extension and to the at least one helical groove, and the first connection part and the second connection part being repeatedly attachable and releasable with each other in a rotatable manner based on the at least one helical groove.

3. The bio-signal apparatus of claim 2, wherein the helical groove of the extension of the first connection part comprises a locking structure at an end of the helical groove in a fastening direction, and the counterpart structure included in the second connection part comprises at least one pin, which is configured to move in the helical groove and lock the first connection part and the second connection part together with the locking structure.

4. The bio-signal apparatus of claim 1, wherein the sheet is structurally integrated with a band attachable round a body part of the mammal, the band comprising the patch electrode structure configured to measure the bio-signal from the body part.

5. The bio-signal apparatus of claim 1, wherein an extension, which is cylindrical, comprises a cavity, which is configured receive, keep and release a battery, and the cavity includes a cavity conductor, which is configured to couple a terminal of the battery with an electrical connector of the first electrical connectors; the first connection part or the second connection part comprises a connection part conductor electrically coupled with another terminal of the battery, and the cavity conductor and the connection part conductor are electrically connected with an electrical circuit of at least one of the first connection part and the second connection part.

6. The bio-signal apparatus of claim 1, wherein the patch electrode structure is structurally integrated with the sheet of the first connection part, the sheet being oblong with tip and tail curved in direction parallel to the normal of the sheet, the normal pointing toward the counterpart electrical connectors.

7. The bio-signal apparatus of claim 1, wherein the sheet of the first connection part comprises a longitudinal extension anatomically fitted to a standard vagina, the longitudinal extension being configured to carry the patch electrode structure configured to receive the bio-signal from pelvic floor muscles of the mammal.

8. A bio-signal apparatus, comprising:

a first connection part, a second connection part and a seal; wherein:

the first connection part comprises a sheet;

the sheet is configured to carry a patch electrode structure, which comprises electrodes configured to receive a bio-signal from a body of a mammal and first electrical connectors, the first electrical connectors being electrically connected with the electrodes;

the second connection part comprises counterpart electrical connectors, the first electrical connectors and the counterpart electrical connectors being repeatedly attachable and releasable with each other to transfer the bio-signal therethrough to data processing;

the seal is configured to seal an interface of the first connection part and the second connection part against dust and moisture, and the seal is configured to surround the first electrical connectors and the electrical counterpart electrical connectors in a continuous manner; and the sheet comprises at least one locking pin and the patch electrode structure has a corresponding hole for each of the at least one locking pin; and each of the at least one locking pin is inserted in a corresponding hole of the at least one hole to keep the sheet and the patch electrode structure in a set position with respect to each other in response to the first connection part and the second connection part being fastened together.

9. The bio-signal apparatus of claim 1, wherein the patch electrode structure comprises a folded section, which comprises an elastic structure within the folded section.

10. The bio-signal apparatus of claim 1, wherein the sheet comprises quick-release fasteners as the first electrical connectors, and the second connection part comprises counterparts to the quick-release fasteners as the second electrical connectors, the quick-release fasteners can be repeatedly fastened and released with their counterparts.

11. The bio-signal apparatus of claim 8, wherein the sheet comprises a cylinder or rod extension, and at least one helical groove on an outer surface of the cylindrical or rod extension, the cylinder or rod extension having a longitudinal axis substantially parallel to a normal of a surface of the sheet;

the second connection part comprises a cylindrical counterpart structure to the cylinder or rod extension and to the at least one helical groove, and the first connection part and the second connection part being repeatedly attachable and releasable with each other in a rotatable manner based on the at least one helical groove.

12. The bio-signal apparatus of claim 11, wherein the helical groove of the extension of the first connection part comprises a locking structure at an end of the helical groove in a fastening direction, and the counterpart structure included in the second connection part comprises the at least one pin, which is configured to move in the helical groove and lock the first connection part and the second connection part together with the locking structure.

13. The bio-signal apparatus of claim 8, wherein the sheet is structurally integrated with a band attachable round a body part of the mammal, the band comprising the patch electrode structure configured to measure the bio-signal from the body part.

14. The bio-signal apparatus of claim 8, wherein an extension, which is cylindrical, comprises a cavity, which is configured receive, keep and release a battery, and the cavity includes a cavity conductor, which is configured to couple a terminal of the battery with an electrical connector of the first electrical connectors; the first connection part or the second connection part comprises a connection part conductor electrically coupled with another terminal of the battery, and the cavity conductor and the connection part conductor are electrically connected with an electrical circuit of at least one of the first connection part and the second connection part.

15. The bio-signal apparatus of claim 8, wherein the second connection part comprises a physical connecting mechanism and second electrical connectors electrically coupled with the counterpart electrical connectors, and the bio-signal apparatus comprises a bio-signal receiver, which comprises receiver electrical connectors, which are counter-connectors to the second electrical connectors, and the second electrical connectors and the receiver electrical connectors are configured to transfer the bio-signal to an electric circuit of the bio-signal receiver to store the bio-signal in at least one memory of the bio-signal receiver.

16. The bio-signal apparatus of claim 8, wherein the patch electrode structure is structurally integrated with the sheet of the first connection part, the sheet being oblong with tip and tail curved in direction parallel to the normal of the sheet, the normal pointing toward the counterpart electrical connectors.

17. The bio-signal apparatus of claim 8, wherein the sheet of the first connection part comprises a longitudinal extension anatomically fitted to a standard vagina, the longitudinal extension being configured to carry the patch electrode structure configured to receive the bio-signal from pelvic floor muscles of the mammal.

18. The bio-signal apparatus of claim 8, wherein the patch electrode structure comprises a folded section, which comprises an elastic structure within the folded section.

19. The bio-signal apparatus of claim 8, wherein the sheet comprises quick-release fasteners as the first electrical connectors, and the second connection part comprises counterparts to the quick-release fasteners as second electrical connectors, the quick-release fasteners can be repeatedly fastened and released with their counterparts.

* * * * *